(12) United States Patent
Fukuda et al.

(10) Patent No.: US 6,348,563 B1
(45) Date of Patent: *Feb. 19, 2002

(54) P-HYDROXYBENZOIC ESTERS, PLASTICIZER CONTAINING THE SAME, POLYAMIDE RESIN COMPOSITION AND MOLDED ARTICLES

(75) Inventors: Hideo Fukuda, Kyoto; Yoshifumi Fujitani, Uji; Ryuichi Kohzu, Kashiba, all of (JP)

(73) Assignee: New Japan Chemical Co., Ltd., Kyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,278
(22) PCT Filed: Feb. 27, 1998
(86) PCT No.: PCT/JP98/00814
  § 371 Date: Aug. 27, 1999
  § 102(e) Date: Aug. 27, 1999
(87) PCT Pub. No.: WO98/38152
  PCT Pub. Date: Sep. 3, 1998

(30) Foreign Application Priority Data

Feb. 28, 1997 (JP) ............................................. 9-062243

(51) Int. Cl.$^7$ .......................... C08K 5/10; C08G 63/00; C08L 77/00; C07C 69/84
(52) U.S. Cl. ....................... 528/310; 528/271; 528/272; 528/288; 528/292; 528/322; 524/292; 524/295; 524/310; 525/420; 525/422; 525/433; 428/34.1; 428/35.2; 264/512; 264/513; 264/514; 264/515; 264/563; 560/1; 560/8; 560/76
(58) Field of Search .................. 560/1, 8, 76; 528/310, 528/271, 272, 288, 292, 322; 524/292, 295, 310; 525/420, 422, 433; 428/34.1, 35.7; 264/512–515, 563

(56) References Cited

U.S. PATENT DOCUMENTS

| 4,245,030 A | 1/1981 | Faust et al. ................. 430/281 |
| 5,324,853 A | 6/1994 | Jones et al. |
| 5,462,986 A | 10/1995 | Bahrmann et al. |

FOREIGN PATENT DOCUMENTS

| JP | 01185362 A | * | 7/1989 |
| JP | 1-185362 | * | 7/1989 |
| JP | 4-356441 | | 12/1992 |
| JP | 6-1913 | | 1/1994 |
| JP | 06166644 A | * | 6/1994 |

* cited by examiner

Primary Examiner—P. Hampton-Hightower
(74) Attorney, Agent, or Firm—Larson & Taylor PLC

(57) ABSTRACT

The present invention provides a p-hydroxybenzoic ester represented by the formula (1)

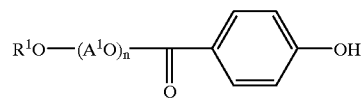

(1)

wherein $R^1$ represents a $C_6$–$C_{10}$ straight-chain or branched-chain alkyl group, $A^1$ represents a $C_2$–$C_4$ alkylene group and n in an integer of 1 to 8, a plasticizer for at least one polyamide resin selected from nylon 11 and nylon 12 which comprises the ester, a polyamide resin composition comprising the ester and at least one polyamide resin selected from nylon 11 and nylon 12, and a polyamide resin molded article comprising the ester and having excellent high-temperature volatilization resistance and low-temperature impact resistance.

10 Claims, No Drawings

P-HYDROXYBENZOIC ESTERS, PLASTICIZER CONTAINING THE SAME, POLYAMIDE RESIN COMPOSITION AND MOLDED ARTICLES

TECHNICAL FIELD

The present invention relates to p-hydroxy-benzoic esters, polyamide resin plasticizers containing said p-hydroxybenzoic esters, and polyamide resin composition and polyamide resin molded articles containing said p-hydroxybenzoic esters.

More particularly, the present invention relates to p-hydroxybenzoic esters which are useful as plasticizers having good compatibility with a polyamide resin selected from the group consisting of nylon 11 and nylon 12, having low volatility, and having an excellent plasticizing effect; polyamide resin compositions containing the same, and polyamide resin molded articles which are obtainable by molding the polyamide resin composition and which have excellent flexibility, reservability, oil resistance, low-temperature impact resistance and high-temperature volatilization resistance.

BACKGROUND ART

Japanese Unexamined Patent Publication No. 1913/1994 filed by the inventors of the present invention broadly discloses a wide variety of p-hydroxybenzoic esters represented by the formula (2)

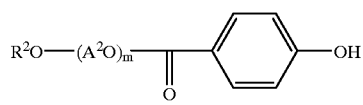

(2)

wherein $R^2$ represents an alkyl group, an alkenyl group, an optionally substituted cycloalkyl group, an aryl group or an aralkyl group; $A^2$ represents a $C_2$–$C_4$ alkylene group; m is an integer of 1 to 20, and discloses that polyamide resin compositions containing said esters are excellent in compatibility at room temperature, good in mechanical properties, and capable of giving excellent molded articles with low-temperature resistance and oil resistance, and are useful as materials for hoses and tubes for automobiles.

More specifically, the publication discloses, as preferable examples of the esters represented by the above formula (2), butoxyethoxyethyl p-hydroxybenzoate, cyclohexyloxy-ethoxyethoxyethyl p-hydroxybenzoate, (p-nonylphenoxyethyl) p-hydroxybenzoate, and the working examples of said publication also disclose the use of butoxyethyl p-hydroxybenzoate and cyclohexyloxyethoxy ethoxyethyl p-hydroxybenzoate.

The above Japanese Unexamined Patent Publication No. 1913/1994 exemplifies a variety of polyamide resins, particularly nylon 6, nylon 66, nylon 610, nylon 11, nylon 12 and copolymerized nylons.

In addition, for evaluating the properties of the molded articles (press sheet) obtained from said polyamide resin composition, the above Japanese Unexamined Patent Publication No. 1913/1994 discloses mechanical properties (tensile strength, elongation at break) evaluation according to ASTM D-638, low-temperature resistance evaluation according to Clash-Berg test, compatibility evaluation by measuring the amount of plasticizer bled out after leaving the press sheet to stand at 25° C. for 48 hours and oil resistance evaluation by measuring the weight loss after immersing the press sheet in gasoline at 25° C. for 48 hours.

Incidentally, due to recent improvement in performance and safety of automobiles, there is an increasing demand for increasing the strength of various parts. Fuel supply tubes and air brake hoses are also required to be more resistant to severe conditions. For example, the temperature of the engine room of a automobile in midsummer may be elevated to nearly 70–80° C., whereas it may be lowered to about –40° C. in winter. Generally, plasticizer in molded articles may volatilize at a high temperature, resulting in impaired physical properties such as mechanical properties and low-temperature resistance, and molded articles may also break upon impact at a low temperature. In order for the molded articles to withstand such environments, it is required that plasticizer does not volatilize at a high temperature (e.g. about 120° C.) out of the molded articles (hereinafter in the present description and claims referred to as "high-temperature volatilization resistance") and that at lower temperatures (e.g. about –40° C.) the molded articles are not broken upon impact (hereinafter in the present description and claims referred to as "low-temperature impact resistance").

However, in the above Japanese Unexamined Patent Publication No. 1913/1994, the properties of the molded article are evaluated in the normal environment. For example, reservability of the esters represented by the formula (2) in polyamide resins is determined based on the compatibility at room temperature. Additionally, the low-temperature resistance of said polyamide resin composition represents the flexible temperature of the resin, and therefore it is not an evaluation of breakage upon impact at lower temperatures.

Accordingly, the Japanese Unexamined Patent Publication No. 1913/1994 in no way gives a hint as to whether the molded article obtainable from the polyamide resin composition disclosed therein is excellent in terms of the above-mentioned high-temperature volatilization resistance and low-temperature impact resistance as recently required by the automobile industry.

DISCLOSURE OF THE INVENTION

It is an object of the present invention to provide a compound useful as a plasticizer which is capable of giving a polyamide resin molded article having excellent properties such as plasticizing ability, compatibility and reservability, particularly having excellent high-temperature volatilization resistance and low-temperature impact resistance, and to further enable the polyamide resin molded article having such excellent properties to be used in a broader range of environments.

The inventors of the present invention carried out extensive research to solve the above-mentioned problems. As a result, the present inventors found that when p-hydroxybenzoic esters, which have a specific structure different from those of the preferable compounds disclosed in the Japanese Unexamined Patent Publication No. 1913/1994, are used as a plasticizer for at least one polyamide resin selected from the group consisting of nylon 11 and nylon 12, there is obtained a molded article which is not only excellent in plasticizing ability, reservability and low-temperature resistance but also excellent in high-temperature volatilization resistance and low-temperature impact resistance. The present invention has been accomplished based on the above findings.

Thus, the present invention provides a p-hydroxybenzoic ester represented by the formula (1)

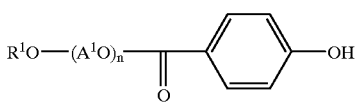

(1)

wherein $R^1$ represents a $C_6$–$C_{10}$ straight-chain or branched-chain alkyl group, $A^1$ represents a $C_2$–$C_4$ alkylene group, and n is an integer of 1 to 8.

The above compound of the formula (1) is not specifically disclosed in the above-mentioned Japanese Unexamined Patent Publication No. 1913/1994, and is a novel compound which acts, with high performance, as a plasticizer for a specific polyamide resin selected from the group consisting of nylon 11 and nylon 12.

The present invention also provides a plasticizer for at least one polyamide resin selected from the group consisting of nylon 11 and nylon 12, the plasticizer comprising a p-hydroxybenzoic ester represented by the above formula (1).

Furthermore, the present invention provides a polyamide resin composition comprising
 (a) at least one polyamide resin selected from the group consisting of nylon and nylon 12; and
 (b) at least one p-hydroxybenzoic ester represented by the formula (1)

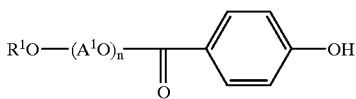

(1)

wherein $R^1$ represents a $C_6$–$C_{10}$ straight-chain or branched-chain alkyl group, $A^1$ represents a $C_2$–$C_4$ alkylene group, and n is an integer of 1 to 8.

The present invention further provides a polyamide resin molded article obtainable by molding the above polyamide resin composition.

The present invention will be described below in detail.

p-Hydroxybenzoic Ester of the Formula (1)

The compound of the formula (1) for use in the present invention is a compound obtainable, for example, by subjecting p-hydroxybenzoic acid and a $C_2$–$C_4$ alkylene oxide adduct of a $C_6$–$C_{10}$ aliphatic alcohol (hereinafter sometimes referred to as "alkoxylated alcohol") to a conventional esterification or ester-interchange reaction.

Examples of the aliphatic alcohol include $C_6$–$C_{10}$ straight-chain or branched-chain aliphatic saturated alcohols or mixtures thereof, specifically, n-hexanol, n-heptanol, n-octanol, 2-ethylhexanol, n-nonyl alcohol, n-decyl alcohol, or mixtures of these alcohols. Examples of the mixtures of these alcohols include a mixture of $C_6$, $C_8$ and $C_{10}$ straight-chain primary alcohols (average number of carbon atoms: 8, trade name "Alfol 610" manufactured by Vista Chemical Far East Co.,Ltd., a mixture of $C_7$, $C_8$ and $C_9$ primary alcohols (containing 80 wt. % of a straight-chain alcohol, average number of carbon atoms: 8, trade name "Linevol 79" manufactured by Shell Chemical Ltd. and a mixture of $C_7$ and $C_9$ primary alcohols (containing 50 wt. % of straight-chain alcohols, average number of carbon atoms: 8, trade name "Diadol 79" manufactured by Mitsubishi Chemical Co.). Among these alcohols, 2-ethylhexanol is recommendable.

When an alcohol having less than 6 carbon atoms is used, the resulting molded article tends to have poor low-temperature impact resistance and high-temperature volatilization resistance. On the other hand, when an alcohol having more than 10 carbon atoms is used, the resulting molded article tends to have poor low-temperature impact resistance.

Examples of $C_2$–$C_4$ alkylene oxide include ethylene oxide (EO), propylene oxide (PO) and butylene oxide (BO), among which recommendable is ethylene oxide.

The number of moles of the alkylene oxide to be added is generally 1 to 8 moles, preferably 2 to 4 moles. When a compound obtainable from an alkoxylated alcohol with more than 8 moles of an alkylene oxide added, the compatibility with the polyamide resin tends to decrease.

In addition, the above alkylene oxides may be used singly or at least two of them may be used in admixture.

The reaction for adding the above alkylene oxide to the aliphatic alcohol may be carried out in a conventional manner, for example, according to the method described in "Jikken Kagaku Kouza 19, Synthesis of Organic Compounds I", edited by The Chemical Society of Japan, published by Maruzen Co., Ltd., Jul. 30, 1957, pages 196–197, by reacting an alkylene oxide with said aliphatic alcohol in the presence of an alkali metal alkoxide such as sodium methoxide as a catalyst, under a normal to an elevated pressure (5 kg/cm$^2$ G) at a temperature. of about 120 to 180° C. Said alkylene oxide is preferably used in an amount corresponding to the desired number of moles of the alkylene oxide to be added, per mole of said aliphatic alcohol. The amount of the catalyst to be used is not particularly limited as far as the reaction can proceed, but it is generally preferable that the amount thereof is about 0.01–0.1 mole per mole of the aliphatic alcohol. This reaction is normally completed in about 1 to 10 hours.

The esterification or ester interchange reaction of the thus obtained alkoxylated alcohol and p-hydroxybenzoic acid can also be carried out by a conventional method, for example, according to the method described in "Plasticizer—its theory and application" authored and edited by Koichi Murai, published by Saiwai Shobo Kabushiki Kaisha, 1973, pages 394–473, by subjecting the alkylene oxide adduct of an aliphatic alcohol and p-hydroxybenzoic acid or its $C_1$–$C_4$ lower alkyl ester to esterification or ester interchange reaction in the presence of dibutyl tin oxide as a catalyst at about 180–200° C. using toluene or xylene as a solvent. In this reaction, it is preferable to use the alkylene oxide-added aliphatic alcohol in an amount of about 1.01–1.2 moles per mole of p-hydroxybenzoic acid or its $C_1$–$C_4$ lower alkyl ester, and to use the catalyst in an amount of about 0.001–0.1 mole per mole of p-hydroxy-benzoic acid or its $C_1$–$C_4$ lower alkyl ester. This reaction is normally completed in about 5 to 20 hours.

In a preferred embodiment of the present invention, it is preferable to use a compound represented by the formula (1) wherein alkylene oxide represented by $A^1$ is ethylene oxide and the number of moles of ethylene oxide added represented by n is 2.

In particular, when a $C_8$ alcohol is used as the aliphatic alcohol, the number of moles of ethylene oxide to be added is preferably 2.

In other words, preferable is the compound represented by the formula (1) wherein $R^1$ is a straight-chain or branched-chain alkyl group having 8 carbon atoms, $A^1$ is ethylene group and n is 2.

Herein, the number of moles of alkylene oxide added in the alkoxylated alcohol is often expressed in average numbers. For example, when the average addition molar number is 2, there is a dispersion in the addition molar numbers, and a co-existing alkoxylated alcohol having a below-average addition molar number (in this case, an alkoxylated alcohol with 1 mole of alkylene oxide added) present therein forms an ester which is more volatile than the ester with 2 moles of alkylene oxide added. On the other hand, esters obtainable from alkoxylated alcohols with above-average addition molar numbers tend to be less compatible with resins than the esters with 2 moles of alkylene oxide added. Therefore, the alkylene oxide addition with the average addition molar number of 2 is different from the alkylene oxide addition with the addition molar number of 2, in terms of plasticizing ability of the resulting esters.

An alkoxylated alcohol having 2 moles of alkylene oxide added can be produced by a method comprising purification, e.g., distillation, of the crude alkoxylated alcohol resulting from the addition of an alkylene oxide. More specifically, the method comprises the steps of reacting 2 moles of an alkylene oxide with the above aliphatic alcohol and removing volatile by-products such as adducts of 1 mole of the alkylene oxide and 1 mole of the aliphatic alcohol from the resulting reaction mixture, e.g., by distillation, giving the desired adducts of 2 moles of the alkylene oxide and 1 mole of the aliphatic alcohol.

In another preferred embodiment of the present invention, also preferable is a mixture of esters represented by the formula (1) wherein the number of moles of the added alkylene oxide, in particular ethylene oxide, is 1 to 8, and the average number of moles of the added alkylene oxide (in particular ethylene oxide) is 4.

Among the compounds represented by the formula (1) of the present invention, preferable are those represented by the formula (1) wherein $R^1$ represents a $C_7$–$C_9$ straight-chain or branched-chain alkyl group, $A^1$ represents a $C_2$ or $C_3$, particularly $C_2$ alkylene group, and n Is 2 to 4.

Among these preferable compounds, examples of particularly preferable p-hydroxybenzoic esters are those represented by the formula (1) wherein $R^1$ represents a $C_8$ alkyl group such as 2-ethylhexyl group. Among them, more preferable are those in which $A^1$ is ethylene group. In this case, it is preferred that n is 2 to 4, particularly 2.

Typical examples of p-hydroxybenzoic esters represented by the formula (1) are as follows:

Hexyloxyethoxyethyl p-hydroxybenzoate;
Hexyloxypropoxypropyl p-hydroxybenzoate;
Hexyloxybutoxybutyl p-hydroxybenzoate;
Octyloxyethoxyethyl p-hydroxybenzoate;
Octyloxypropoxypropyl p-hydroxybenzoate;
Octyloxybutoxybutyl p-hydroxybenzoate;
2'-Ethylhexyloxyethoxyethyl p-hydroxybenzoate;
2'-Ethylhexyloxypropoxypropyl p-hydroxybenzoate;
2'-Ethylhexyloxybutoxybutyl p-hydroxybenzoate;
Decyloxyethoxyethyl p-hydroxybenzoate;
Decyloxypropoxypropyl p-hydroxybenzoate;
Decyloxybutoxybutyl p-hydroxybenzoate;
Esters of p-hydroxybenzoic acid and a mixture (average addition molar number of EO=4) of EO adducts (addition molar number of EO=1–8) of hexanol;
Esters of p-hydroxybenzoic acid and a mixture (average addition molar number of EO=4) of EO adducts (addition molar number of EO=1–8) of octanol;
Esters of p-hydroxybenzoic acid and a mixture (average addition molar number of EO=4) of EO adducts (addition molar number of EO=1–8) of 2-ethylhexanol; and Esters of p-hydroxybenzoic acid and a mixture (average addition molar number of EO=4) of EO adducts (addition molar number of EO=1–8) of decanol.

Among these, more preferable examples are 2'-ethylhexyloxyethoxyethyl p-hydroxybenzoate, esters of p-hydroxybenzoic acid and a mixture (average addition molar number of EO=4) of EO adducts of 2-ethylhexanol (addition molar number of EO=1–8).

The compound represented by the formula (1) of the present invention is useful as a plasticizer for polyamide resins, in particular, for at least one polyamide resin selected from the group consisting of nylon 11 and nylon 12.

For producing a polyamide resin molded article having excellent low-temperature impact resistance, at least 1 mole of an alkylene oxide should be present, as added, between the alkyl chain and the p-hydroxybenzoic acid moiety of the p-hydroxybenzoic ester. For producing a polyamide resin molded article having excellent high-temperature volatilization resistance, its alkyl chain needs to have 6 or more carbon atoms.

However, the esters wherein the number of moles of an alkylene oxide added is 9 or more or wherein the alkyl chain has 11 or more carbon atoms tend to be less compatible with the polyamide resins. In addition, there is a tendency that as the number of carbon atoms in the alkyl chain increases, oil resistance decreases. To impart all of the characteristics of low-temperature impact resistance, high-temperature volatilization resistance and compatibility with polyamide resins as well as oil resistance, the number of carbon atoms in the alkyl chain should be 6 to 10, preferably 7 to 9, and the number of moles of an alkylene oxide added should be 1 to 8, preferably 1 to 4.

Plasticizer Containing the Compound of the Formula (1)

As mentioned above, the p-hydroxybenzoic acid represented by the formula (1) is useful for a plasticizer for at least one polyamide resin selected from the group consisting of nylon 11 and nylon 12 in particular.

Therefore, the present invention provides a plasticizer for at least one polyamide resin selected from the group consisting of nylon 11 and nylon 12, the plasticizer containing a p-hydroxybenzoic acid represented by the formula (1).

The p-hydroxybenzoic ester represented by the formula (1) can be used in combination with other plasticizers known in the art, such as N-butylbenzene-sulfonamide and 2-ethylhexyl p-hydroxybenzoate. In this case, the p-hydroxybenzoic ester represented by the formula (1) is preferably used in a greater amount than said known plasticizers, i.e., in an amount equal to or greater than the amount of said known plasticizer, in particular, twice the weight of said known plasticizer. In other words, when used in combination with said known plasticizers, the ester represented by the formula (1) is preferably used in an amount of 50 wt. % or higher, particularly in the range of 67 wt. % to 99 wt. %, based on the total amount of the ester represented by the formula (1) and said other plasticizer.

The amount of the plasticizer comprising the p-hydroxybenzoic ester represented by the formula (1) is suitably selected according to the intended use. Typically, the amount of the plasticizer, calculated as the ester represented by the formula (1), is about 1–50 wt. parts, preferably about 5–30 wt. parts, per 100 wt. parts of the polyamide resin (nylon 11 and/or nylon 12). If the amount is less than 1 wt. part, it is hard to produce a plasticizing effect, while the amount more than 50 wt. parts tends to increase the degree of bleeding thereof to the surface of the resin.

Polyamide Resin Composition

The polyamide resin composition of the present invention comprises (a) at least one polyamide resin selected from the group consisting of nylon 11 and nylon 12, and (b) the p-hydroxybenzoic ester represented by the formula (1).

The polyamide resin to be used in the present invention is nylon 11 and/or nylon 12. Nylon 11 and nylon 12 may be used singly or in combination. In either case, they can be used in a commonly available form, such as powder, pellets, etc.

The amount of p-hydroxybenzoic ester represented by the formula (1) may be suitably selected according to the intended use. Typically, the amount of the ester represented by the formula (1) is about 1–50 wt. parts, preferably about 5–30 wt. parts, per 100 wt. parts of the polyamide resin (nylon 11 and/or nylon 12). If the amount is less than 1 wt. part, it is hard to produce a plasticizing effect, while the amount of more than 50 wt. parts tends to increase the degree of bleeding thereof to the surface of the resin.

As described above, the p-hydroxybenzoic ester represented by the formula (1) may be used in combination with other plasticizers known in the art, such as N-butyl-benzenesulfonamide, 2-ethylhexyl p-hydroxybenzoate, etc. In this case, p-hydroxybenzoic ester represented by the formula (1) is preferably used in a greater amount than said known plasticizers, i.e., in an amount equal to or greater than the amount of said known plasticizer, in particular, twice the weight of the said known plasticizer. In other words, when used in combination with said known plasticizers, the ester represented by the formula (1) is preferably used in an amount of 50 wt. % or higher, particularly in the range of 67 wt. % to 99 wt. %, based on the total amount of the ester represented by the formula (1) and said other plasticizer.

The polyamide resin composition according to the present invention may optionally contain additives such as stabilizers, surfactants, colorants, lubricants, fillers, antioxidants, ultraviolet absorbers and antistatic agents, in an amount which does not adversely affect the invention.

Example of the stabilizers include trisnonyl-phenylphosphite, diphenylisodecylphosphite, triphenyl-phophate, tris(2,4-di-tert-butylphenyl)phosphate and like phosphoric acid compounds; N,N'-hexamethylene bis(3,5-di-tert-butyl-4-hydroxyhydrocyanamide), 1,3,5-trimethyl-2, 4,6-tris(3,5-di-tert-butyl-4-hydroxybenzyl)benzene, 2,6-di-tert-butylphenol, tetrakis[methylene-3-(3',5'-di-tert-butyl-4'-hydroxy-phenyl)propionato]methane, 2-hydroxy-4-methoxybenzophenone and like phenol compounds. The amount of these stabilizers to be added is, for example, 0.01 to 2 wt. parts per 100 wt. parts of at least one polyamide resin selected from the group consisting of nylon 11 and nylon 12.

Examples of the surfactants include glycerin fatty acid esters, polyoxyethylene sorbitan fatty acid ($C_{12}$–$C_{18}$) esters, polyethylene glycol fatty acid ($C_8$–$C_{22}$) esters, polyoxyethylenealkyl ($C_7\leqq$, particularly $C_7$–$C_{22}$) phenyl ethers, polyoxypropylene polyoxyethylene block copolymers, polyethylene glycols, polypropylene glycols and like nonionic surfactants; and salts (sodium, potassium, ammonium) of fatty acids ($C_8$–$C_{22}$) and like anionic surfactants. The amount of the surfactants to be used is, for example, 0.1 to 2 wt. parts per 100 wt. parts of at least one polyamide resin selected from the group consisting of nylon 11 and nylon 12.

Examples of the colorants include carbon black, titanium yellow, cobalt blue, ultramarine blue and other various dyes. The amount of the colorants to be used is, for example, 0.1 to 1 wt. part per 100 wt. parts of at least one polyamide resin selected from the group consisting of nylon 11 and nylon 12.

Examples of the lubricants include liquid paraffin, hydrogenated polybutene and like aliphatic hydrocarbons; stearic acid and like $C_8$–$C_{22}$ higher fatty acids; salts (aluminum, calcium, magnesium, zinc) of $C_8$–$C_{22}$ higher fatty acid; $C_4$–$C_{18}$ aliphatic alcohols, esters of montanic acid and ethanediol or 1,3-butandiol, rice bran wax and like fatty acid esters of monohydric or polyhydric alcohols; hydrogenated castor oil, acetylated monoglycerides, polyethylene wax and like triglycerides and waxes; ethylene-bis-fatty acid ($C_{16}$–$C_{18}$) amide, fatty acid ($C_8$–$C_{22}$) amide and like higher fatty acid amides; dimethylpolysiloxane, methylphenylpolysiloxane and like silicone oils; and montanic acid salts (sodium, calcium). The amount of the lubricants to be added is, for example, 0.1 to 3 wt. parts per 100 wt. parts of at least one polyamide resin selected from the group consisting of nylon 11 and nylon 12.

Examples of the fillers include magnesium oxide, aluminum oxide, silicon oxide, titanium oxide, chromium oxide, iron oxide, zinc oxide and like oxides; magnesium hydroxide, aluminum hydroxide and like hydroxides; magnesium carbonate, calcium carbonate and like carbonates; barium sulfate and like sulfates; magnesium silicate, calcium silicate and like silicates; fibers and powders of silica, alumina, clay, talc, diatomaceous earth, glass, metal, carbon and the like; glass balls and graphite. The amount of the fillers to be added is, for example, 1 to 50 wt. parts per 100 wt. parts of at least one polyamide resin selected from the group consisting of nylon 11 and nylon 12.

Examples of the antioxidants include alkyl disulfide, thiodipropionic acid ester, benzothiazole and like sulfur-based compounds; zinc dialkyldithiophosphate, zinc diaryldithiophosphate and like organometallic compounds. The amount of the antioxidants to be added is, for example, 0.01 to 2 wt. parts per 100 wt. parts of at least one polyamide resin selected from the group consisting of nylon 11 and nylon 12.

Examples of the ultraviolet absorbers include phenyl salicylate, p-tert-butylphenylsalicylate and like salicylate-based compounds; 2-hydroxy-4-n-octoxybenzophenone, 2-hydroxy-4-methoxybenzophenone and like benzophenone-based compounds; 5-methyl-1H-benzotriazole, 1-dioctylaminomethylbenzotriazole, 2-(2'-hydroxy-3'-tert-butyl-5'-methylphenyl)-5-chlorobenzotriazole and like benzotriazole-based compounds; and additionally cyanoacrylate-based compounds. The amount of the ultraviolet absorbers to be added is, for example, 0.01 to 2 wt. parts per 100 wt. parts of at least one polyamide resin selected from the group consisting of nylon 11 and nylon 12.

Examples of antistatic agents are anionic antistatic agents of the alkylsulfonate type, alkyl ether carboxylic acid type or dialkylsulfosuccinate type; nonioic antistatic agents such as polyethylene glycol derivatives, sorbitan derivatives, diethanolamine derivatives and the like; cationic antistatic agents such as quaternary ammonium salts of the alkyl amide amine type, alkyl dimethyl benzyl type and the like, organic acid salts or hydrochloride of the alkylimidazoline type, alkylpyridinium type and the like; and amphoteric antistatic agents of the alkyl betaine type, alkylimidazoline type and the like. The amount of the antistatic agents to be added is, for example, 0.1 to 2 wt. parts per 100 wt. parts of at least one polyamide resin selected from the group consisting of nylon 11 and nylon 12.

For adding the p-hydroxybenzoic ester represented by the formula (1) to at least one polyamide selected from the group consisting of nylon 11 and nylon 12, any known method may be selected. For example, there may be employed a method comprising the steps of mixing the desired amount of the ester and if desired one or more of the above additives with a powder or pellets of the polyamide in a mixer at a temperature not higher than the softening point of the polyamide (e.g., about 20–80° C., particularly about 40–60° C.); extruding the mixture at a temperature not lower than the softening point of the polyamide (e.g., about 180–260° C., particularly about 200–240° C.); cooling the extrudate, for example, with water; and cutting the cooled extrudate to obtain pellets. Alternatively, there may be employed a method in which said ester and if desired one or more additives may be added to and mixed with monomers prior to polyamide polymerization or in the course of polymerization.

Polyamide Resin Molded Article

The thus obtained polyamide resin composition may be molded by conventionally known methods such as injection molding, extrusion molding, powder molding, blow molding, press molding or the like.

The conditions for molding may be similar to those employed commonly. Taking injection molding as an example, the conditions may be molten resin temperature of 235° C., mold temperature of 80° C., primary pressure of 650 kgf/cm$^2$, secondary pressure of 600 kgf/cm$^2$ and back pressure of 100 kgf/cm$^2$.

The thus obtained molded article has a variety of excellent properties, particularly high-temperature volatilization resistance and low-temperature impact resistance. For instance, the molded articles are suitable for hoses and tubes used in general machine parts and automobile parts. Specifically, tubes for fuel supply, hydraulic system, air pressure system or the like used in industrial robots, constructional machines or the like can be mentioned as the general machine parts, and tubes for fuels supply and hoses for air braking system can be mentioned as the automobile parts.

Additionally, the molded articles are useful not only as the general machine parts, hoses and tubes for automobile parts, but also as constructional parts, textile machine parts, materials for containers and packaging, sundries, materials for extrusion products such as films, tubes, round bars, sheets and monofilaments, and coating agents.

EXAMPLES

Described below are some production examples of the esters represented by the formula (1).

Production Example 1

Production of 2'-ethylhexyloxyethoxyethyl p-hydroxybenzoate

In a 1 L 3-necked flask was placed 138 g (1.0 mole) of p-hydroxybenzoic acid, 239.8 g (1.1 mole) of 2-ethylhexyloxyethoxyethyl alcohol (manufactured by Nihon Nyukazai Kabushiki Kaisha, trade name "EHDG"), 1.1 g of dibutyl tin oxide and 11 g of toluene. The mixture was heated in a stream of nitrogen with stirring. While water formed was removed, in the form of an azeotropic mixture with toluene, from the reaction system, the mixture was heated to 190° C. The mixture was maintained at 190° C. for 8 hours until the acid value of the reaction mixture became 1 mgKOH/g or below.

Then, the mixture was stirred at reduced pressure of not higher than 5 mmHg at 190° C. for 1 hour and then at 210° C. for 30 minutes. Excess alcohol was removed therefrom. The mixture was cooled and filtered, affording 311 g (yield: 91%) of the ester as a clear pale yellow liquid. The characteristic values of the resulting title ester are shown in Table 1.

Production Example 2

Production of ester of a mixture of ethylene oxide (1–8 moles) adducts of 2-ethylhexyl alcohol (average number of moles of EO added=4) and p-hydroxybenzoic acid The procedure of Production Example 1 was followed with the exception of using 138 g (1.0 mole) of p-hydroxybenzoic acid, 321.3 g (1.05 mole) of a mixture of ethylene oxide (1–8 moles) adducts of 2-ethylhexyl alcohol (average number of moles of EO added: 4)(manufactured by Nihon Nyukazai Kabushiki Kaisha, trade name "NEWCOL-1004"), 2.3 g of dibutyl tin oxide and 14 g of toluene, thereby affording 362 g (yield: 85%) of the title ester as a clear pale yellow liquid. The characteristic values of the title ester obtained are shown in Table 1.

TABLE 1

| Characteristic value | Production Example 1 | Production Example 2 |
|---|---|---|
| Color number (APHA) | 120 | 150 |
| Specific gravity (25° C./4° C.) | 1.06 | 1.02 |
| Acid value (mgKOH/g) | 0.65 | 0.88 |
| Viscosity (25° C., cP) | 1300 | 1100 |
| Ester value (mgKOH/g) | 162 | 128 |
| IR (cm$^{-1}$) (neat) | 3333, 2959 1715, 1610 1593, 1278 1166, 1099 772 | 3332, 2959 1719, 1611 1595, 1279 1169, 775 |

Remarks:
Color number (APHA): measured according to JIS K-4101
Acid value and ester value: measured according to JIS K-0070
Specific gravity: measured according to JIS K-1527
Viscosity: measured according to JIS K-2283
IR: measured by 2000FT-IR manufactured by Perkin-Elmer Corporation Reference Example 1

Production of 2-ethylhexyloxybutoxybutyl alcohol

In a 2 L autoclave was placed 130.2 g (1.0 mole) of 2-ethylhexanol, 144.2 g (2.0 moles) of butylene oxide and 0.3 g of NaOEt. N$_2$ was bubbled through the mixture and water was removed therefrom. Then the mixture was subjected to esterification at a pressure of 5 kg/cm$^2$G and at a temperature of 150° C. for 2 hours. Further, aging reaction was carried out at a pressure of 5 kg/cm$^2$G and at a temperature of 155° C. until the pressure change of the autoclave was no more observed.

After cooling the mixture, the catalyst NaOEt was neutralized by a 1N—HCl solution, and a precipitate was filtered. The resulting crude reaction product was distilled under reduced pressure to thereby produce 29.7 g of 2-ethylhexyloxybutoxybutyl alcohol as a colorless liquid in a yield of 10%.

Production Example 3

Production of 2'-ethylhexyloxybutoxybutyl p-hydroxybenzoate

Following the procedure of Production Example 1 with the exception of using 2-ethylhexyloxybutoxybutyl alcohol produced in Reference Example 1 as alkoxylated alcohol, 281 g (yield: 73%) of 2'-ethylhexyloxybutoxybutyl p-hydroxybenzoate was obtained.

Production Examples 4 and 5

Following the procedure of Production Examples 1 to 3, various esters shown in Table 2 below were produced using the materials (alcohol and ethylene oxide (EO)) shown in Table 2 below.

The thus obtained esters were identified by their acid value (determined according to JIS K-0070), ester value (JIS K-0070) and IR (determined by 2000FT-IR manufactured by Perkin Elmer Corporation).

TABLE 2

| Production Example | Alcohol | Number of moles of EO | Ester |
|---|---|---|---|
| 4 | n-Hexanol | 2 | Hexyloxyethoxyethyl p-hydroxybenzoate |
| 5 | n-Decanol | 2 | Decyloxyethoxyethyl p-hydroxybenzoate |

The present invention will hereinafter be illustrated with reference to Examples showing the performance of the ester represented by the formula (1) as a plasticizer, and Comparative Examples wherein other plasticizers than the ester represented by the formula (1) are used.

In the following Examples and Comparative examples, resin compositions and press sheets were produced by the following methods:

Production of Resin Composition

Nylon 11 or nylon 12 and a plasticizer were kneaded at 230° C. using a laboplasto mill. The resin composition was extruded by nitrogen purging. Then the extrudate was cooled with water and cut into pellets with a pelletizer.

Production of Press Sheet

The above-mentioned resin composition (pellets) were hot-pressed at 210° C. using a press molding machine, giving a 1-mm thick sheet measuring 200 mm×250 mm.

The properties of the press sheets produced from the resin composition by the aforementioned method in each of the Examples and Comparative Examples were measured and evaluated according to the following methods.

Compatibility

The press sheet was left to stand for 48 hours in a room having a constant temperature of 25° C. and a constant relative humidity of 60%. The amount of a plasticizer which bled out onto the surface of the sheet was visually inspected, and the compatibility of the plasticizer with resins and reservability in the composition were evaluated in accordance with the following criteria.

○: No bleeding

Δ: Slight bleeding

×: The surface is wet because of the plasticizer bled out

Mechanical Properties

The flexural strength and flexural modulus were determined according to ASTM D-790, and the tensile elongation at break was determined according to ASTM D-638, thereby evaluating the plasticizing ability.

Low-temperature Resistance

The low-temperature flexibility of the sheet was evaluated according to Clash-Berg method (ASTM-D-1043).

The lower the flexible temperature, the higher the low-temperature resistance.

Low-temperature Impact Resistance

The press sheet, which had been or had not been heated in a Geer oven at 110° C. for 24 hours, was cooled to −40° C. A 1,000 g weight was dropped onto the sheet from the height of 45 cm. The impact resistance at a low temperature was determined by the numbers of broken sheets out of 10 sheets.

The less the number of broken sheets, the better the low-temperature resistance. If any of the sheets is ever broken, a serious problem may be posed in terms of safety (e.g., for use as automobile parts) and is not suitable for practical use.

High-temperature Volatilization Resistance

The percent weight loss (weight %) of the test piece was measured before and after being heated in a Geer oven at 120° C. for 7 days so as to evaluate the volatilization resistance of the plasticizer during heating.

The lower the percent weight loss value, the higher the volatilization resistance.

Oil Resistance

The press sheet was immersed in gasoline at 25° C. for 48 hours, and the percent weight loss (weight %) of the press sheet before and after the immersion was determined to evaluate the oil resistance thereof.

The lower the percent weight loss value, the higher the oil resistance.

In the following Examples and Comparative Examples, the following polyamide resins were used:

Nylon 12: Trade name "UBE nylon 3030B" (manufactured by Ube Industries Ltd.)

Nylon 11: Trade name "Rilsan nylon 11 BESN O TL" (manufactured by Toray Industries, Inc.)

Example 1

A polyamide resin composition was prepared using 100 wt. parts of nylon 12 and 15 wt. parts of 2'-ethylhexyloxyethoxyethyl p-hydroxybenzoate (hereinafter referred to as "Compound 1", and a press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 3.

Example 2

A polyamide resin composition was prepared using 100 wt. parts of nylon 12 and 15 wt. parts of an ester (hereinafter referred to as "Compound 2") of a mixture of ethylene oxide (1–8 moles) adducts of 2-ethylhexyl alcohol (average number of moles of EO added=4) and p-hydroxybenzoic acid. A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 3.

Example 3

A polyamide resin composition was prepared using 100 wt. parts of nylon 12 and 15 wt. parts of 2'-ethylhexyloxybutoxybutyl p-hydroxybenzoate (hereinafter referred to as "Compound 3"). A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 3.

Example 4

A polyamide resin composition was prepared using 100 wt. parts of nylon 12 and 15 wt. parts of hexyloxyethoxyethyl p-hydroxybenzoate (hereinafter referred to as "Compound 4"). A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 3.

Example 5

A polyamide resin composition was prepared using 100 wt. parts of nylon 12 and 15 wt. parts of decyloxyethoxyethyl p-hydroxybenzoate (hereinafter referred to as "Compound 5"). A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 3.

With respect to the obtained press sheet, compatibility, mechanical property, low-temperature resistance, low-temperature impact resistance, high-temperature volatilization resistance and oil resistance were evaluated. The results are shown in Table. 4.

Comparative Example 3

A polyamide resin composition was prepared using 100 wt. parts of nylon 12 and 15 wt. parts of pentyloxyethoxyethyl p-hydroxybenzoate (hereinafter referred to as "Compound 7"). A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 4.

TABLE 3

| | Example | | | | |
|---|---|---|---|---|---|
| | 1 | 2 | 3 | 4 | 5 |
| Polyamide resin | Nylon 12 | Nylon 12 | Nylon 12 | Nylon 12 | Nylon 12 |
| Plasticizer | Compound 1 | Compound 2 | Compound 3 | Compound 4 | Compound 5 |
| Amount (wt. part) | 15 | 15 | 15 | 15 | 15 |
| Compatibility | ◯ | ◯ | ◯ | ◯ | ◯ |
| Mechanical property | | | | | |
| Flexural strength, Mpa | 19 | 18 | 19 | 19 | 18 |
| Flexural modulus, Mpa | 400 | 390 | 390 | 400 | 410 |
| Tensile elongation at break, % | 350 | 350 | 360 | 350 | 360 |
| Low-temperature resistance | | | | | |
| Flexible temperature, ° C. | −16.0 | −15.5 | −14.0 | −13.0 | −14.5 |
| Low-temperature impact resistance (number of breakage) | | | | | |
| Untreated | 0 | 0 | 0 | 0 | 0 |
| Heat-treated | 0 | 0 | 0 | 0 | 0 |
| High-temperature voltilization resistance, Percent weight loss | 2.3 | 2.1 | 2.0 | 2.9 | 1.9 |
| Oil resistance, Percent weight loss | 0.71 | 0.69 | 0.85 | 0.71 | 0.90 |

The results of Examples 1 to 5 reveal that the press sheets produced from the polyamide resin composition containing nylon 12 and p-hydroxybenzoic ester represented by the formula (1) have excellent properties (compatibility, mechanical property, low-temperature resistance, oil resistance), and further very low volatility at higher temperatures and good low-temperature impact resistance.

Comparative Example 1

A polyamide resin composition was prepared using 100 wt. parts of nylon 12 and 15 wt. parts of 2-ethylhexyl p-hydroxybenzoate (hereinafter abbreviated as "EHPB"). A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 4.

Comparative Example 2

A polyamide resin composition was prepared using 100 wt. parts of nylon 12 and 15 wt. parts of butoxyethyl p-hydroxybenzoate (hereinafter referred to as "Compound 6"). A press sheet was produced from the composition.

Comparative Example 4

A polyamide resin composition was prepared using 100 wt. parts of nylon 12 and 15 wt. parts of cyclohexyloxyethoxyethyl p-hydroxybenzoate (hereinafter referred to as "Compound 8"). A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 4.

Comparative Example 5

A polyamide resin composition was prepared using 100 wt. parts of nylon 12 and 15 wt. parts of undecyloxyethoxyethyl p-hydroxybenzoate (hereinafter referred to as "compound 9"). A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 4.

TABLE 4

|  | Comparative Example | | | | |
|---|---|---|---|---|---|
|  | 1 | 2 | 3 | 4 | 5 |
| Polyamide resin | Nylon 12 | Nylon 12 | Nylon 12 | Nylon 12 | Nylon 12 |
| Plasticizer | EHPB | Compound 6 | Compound 7 | Compound 8 | Compound 9 |
| Amount (wt. part) | 15 | 15 | 15 | 15 | 15 |
| Compatibility | ○ | ○ | ○ | ○ | ○ |
| Mechanical property | | | | | |
| Flexural strength, MPa | 19 | 18 | 18 | 18 | 18 |
| Flexural modulus, Mpa | 430 | 390 | 410 | 410 | 390 |
| Tensile elongation at break, % | 350 | 350 | 340 | 340 | 350 |
| Low-temperature resistance | | | | | |
| Flexible temperature, °C. | −11.5 | −12.5 | −14.0 | −14.5 | −13.0 |
| Low-temperature impact resistance (number of breakage) | | | | | |
| Untreated | 5 | 3 | 1 | 2 | 1 |
| Heat-treated | 2 | 1 | 1 | 1 | 1 |
| High-temperature volatilization resistance, Percent weight loss | 12.0 | 11.8 | 3.2 | 4.3 | 1.8 |
| Oil resistance, Percent weight loss | 1.41 | 0.70 | 0.70 | 0.62 | 0.95 |

The results of Comparative 1 reveal that p-hydroxybenzoic ester with no alkylene oxide added is highly volatile at a higher temperature and has low oil resistance. On the other hand, Comparative Examples 2 to 5 show that the molded article containing an ester of p-hydroxybenzoic acid and an ethylene oxide adduct of an aliphatic alcohol having an alkyl chain other than a $C_6$–$C_{10}$ straight-chain or branched-chain alkyl, has an inferior low temperature and high-temperature volatilization resistance if the alkyl moiety derived from the aliphatic alcohol has 5 or less carbon atoms (Comparative examples 2 and 3). Even when said alkyl moiety has 6 or more carbon atoms, low-temperature impact resistance and high-temperature volatilization resistance are poor if the alkyl moiety is a cycloalkyl group.

These results show that the molded article containing the ester represented by the formula (1) wherein $R^1$ represents a $C_6$–$C_{10}$ straight-chain or branched-chain alkyl group and 1 to 8 moles of an alkylene oxide has been added is excellent in terms of both high-temperature volatilization resistance and low-temperature impact resistance.

Example 6

A polyamide resin composition was prepared using 100 wt. parts of nylon 11 and 15 wt. parts of "Compound 1". A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 5.

Example 7

A polyamide resin composition was prepared using 100 wt. parts of nylon 11 and 15 wt. parts of "Compound 2". A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 5.

Comparative Example 6

A polyamide resin composition was prepared using 100 wt. parts of nylon 11 and 15 wt. parts of "Compound 6". A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 5.

Comparative Example 7

A polyamide resin composition was prepared using 100 wt. parts of nylon 11 and 15 wt. parts of "Compound 7". A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 5.

Comparative Example 8

A polyamide resin composition was prepared using 100 wt. parts of nylon 11 and 15 wt. parts of "Compound 8". A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 5.

Comparative Example 9

A polyamide resin composition was prepared using 100 wt. parts of nylon 11 and 15 wt. parts of "Compound 9". A press sheet was produced from the composition.

With respect to the obtained press sheet, compatibility, mechanical property, low-temperature resistance, low-temperature impact resistance, high-temperature volatilization resistance and oil resistance were evaluated. The results are shown in Table 5.

TABLE 5

| | Example | | Comparative Example | | | |
|---|---|---|---|---|---|---|
| | 6 | 7 | 6 | 7 | 8 | 9 |
| Polyamide resin | Nylon 11 | Nylon 11 | Nylon 11 | Nylon 11 | Nylon 11 | Nylon 11 |
| Plasticizer | Compound 1 | Compound 2 | Compound 6 | Compound 7 | Compound 8 | Compound 9 |
| Amount (wt. part) | 15 | 15 | 15 | 15 | 15 | 15 |
| Compatibility | ○ | ○ | ○ | ○ | ○ | ○ |
| Mechanical property | | | | | | |
| Flexural strength, MPa | 22 | 21 | 21 | 21 | 22 | 22 |
| Flexural modulus, MPa | 330 | 320 | 340 | 340 | 350 | 330 |
| Tensile elongation at break, % | 320 | 320 | 310 | 310 | 310 | 320 |
| Low-temperature resistance | | | | | | |
| Flexible temperature, °C. | −17.0 | −16.5 | −7.0 | −12.5 | −11.5 | −13.0 |
| Low-temperature impact resistance (number of breakage) | | | | | | |
| Untreated | 0 | 0 | 2 | 1 | 2 | 1 |
| Heat-treated | 0 | 0 | 1 | 1 | 1 | 1 |
| High-temperature volatilization resistance, Percent weight loss | 2.1 | 2.0 | 11.5 | 3.1 | 4.1 | 1.6 |
| Oil resistance, Percent weight loss | 0.70 | 0.69 | 0.69 | 0.70 | 0.60 | 0.92 |

Examples 6 and 7 are the examples of polyamide resin compositions containing nylon 11 and the ester represented by the formula (1). The molded articles obtained from the compositions exhibit excellent low-temperature impact resistance and high-temperature volatilization resistance.

On the other hand, Comparative Examples 6 to 9 are the examples of nylon 11 containing a plasticizer of p-hydroxybenzoic acid alkoxy ester whose alkyl chain is not a $C_6$–$C_{10}$ straight-chain or branched-chain alkyl. All of the compositions exhibit inferior high-temperature volatilization resistance and low-temperature impact resistance.

The summary of the results in Tables 3 to 5 is as follows:

As seen from the results of Examples 1 to 7, addition of the ester represented by the formula (1) wherein $R^1$ represents a $C_6$–$C_{10}$ straight-chain or branched-chain alkyl group to a polyamide resin provides a resin molded article having good low-temperature impact resistance (number of press sheet breakage at a lower temperature: 0) and high-temperature volatilization less than 3 wt. %) without impairing its plasticity.

On the other hand, the use of the ester of Comparative Example 1 with no alkylene oxide added or the ester of an alkylene oxide adduct of straight-chain aliphatic alcohol having 5 or less carbon atoms and p-hydroxybenzoic acid used in Comparative Examples 2 and 3 or Comparative Example 6 and 7 give molded articles having poor low-temperature impact resistance and high-temperature volatilization resistance. In addition, the use of the ester of an alkylene oxide adduct of cyclic alcohol having 6 carbon atoms and p-hydroxybenzoic acid (Comparative Examples 4 and 8), and the use of the ester of an alkylene oxide adduct of straight-chain alcohol having more than 10 carbon atoms and p-hydroxybenzoic acid (Comparative Examples 5 and 9) imparts an improved high-temperature volatilization resistance but leads to an inferior low-temperature impact resistance (number of press sheet breakage: 1 or more). Considering the balance of all the characteristics such as mechanical property, low-temperature resistance, low-temperature impact resistance, high-temperature volatilization resistance, oil resistance and the like, the ester represented by the formula (1) wherein $R^1$ has 8 carbon atoms is the most excellent among others.

INDUSTRIAL APPLICABILITY

By blending the ester of an alkylene oxide adduct of an aliphatic saturated alcohol and p-hydroxybenzoic acid represented by the formula (1) according to the invention with at least one polyamide resin selected from the group consisting of nylon 11 and nylon 12, a polyamide resin composition having excellent physical properties such as plasticity, high-temperature volatilization resistance and low-temperature impact resistance can be provided.

What is claimed is:

1. 2′-ethylhexyloxyethoxyethyl p-hydroxybenzoate.

2. A polyamide resin composition giving a molded article with volatilization resistance and impact resistance, the composition comprising
    (a) at least one polyamide resin selected from the group consisting of nylon 11 and nylon 12; and
    (b) a p-hydroxybenzoic ester represented by the formula (1)

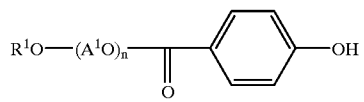

(1)

wherein $R^1$ represents a $C_6$–$C_{10}$ straight-chain or branched-chain alkyl group, $A^1$ represents a $C_2$–$C_4$ alkylene group, and n is an integer of 1 to 8.

3. The polyamide resin composition according to claim 2, wherein said p-hydroxybenzoic ester is a compound represented by the formula (1), wherein $R^1$ represents a $C_8$ straight-chain or branched-chain alkyl group, $A^1$ represents a $C_2$ alkylene group, and n is an integer of 2 to 4.

4. The polyamide resin composition according to claim 3, wherein said p-hydroxybenzoic ester is at least one member selected from the group consisting of 2′-ethylhexyloxyethoxyethyl p-hydroxybenzoate and esters of p-hydroxybenzoic acid and a mixture (average addition molar number of EO=4) of EO adducts (addition molar number of EO=1–8) of 2-ethylhexanol.

5. The polyamide resin composition according to claim 2, wherein said p-hydroxybenzoic ester is 2′-ethylhexyloxyethoxyethyl p-hydroxybenzoate.

6. The polyamide resin composition according to claim 2, wherein said p-hydroxybenzoic ester is present in an amount of 1 to 50 wt. parts per 100 wt. parts of said polyamide resin.

7. The polyamide resin composition according to claim 2, which is intended for producing hoses and tubes.

8. A molded article having volatilization resistance and impact resistance, comprising (a) at least one polyamide resin selected from the group consisting of nylon 11 and nylon 12; and (b) a p-hydroxybenzoic ester represented by the formula (1)

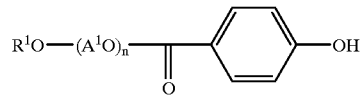

(1)

wherein $R^1$ represents a $C_6$–$C_{10}$ straight-chain or branched-chain alkyl group, $A^1$ represents a $C_2$–$C_4$ alkylene group, and n is an integer of 1 to 8.

9. The molded article according to claim 8 which is hoses or tubes.

10. A method for imparting volatilization resistance and impact resistance to a molded article comprising at least one polyamide resin selected from nylon 11 and nylon 12, the method comprising the steps of blending at least one p-hydroxybenzoic ester represented by the formula (1)

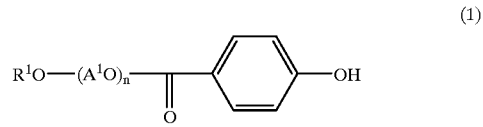

(1)

wherein $R^1$ represents a $C_6$–$C_{10}$ straight-chain or branched-chain alkyl group, $A^1$ represents a $C_2$–$C_4$ alkylene group, and n is an integer of 1 to 8, with at least one polyamide resin selected from the group consisting of nylon 11 and nylon 12, and molding the resin composition.

* * * * *